United States Patent [19]

Maillard et al.

[11] Patent Number: 4,556,674

[45] Date of Patent: Dec. 3, 1985

[54] 2-IMINO-PYRROLIDINES, PROCESS FOR THEIR PREPARATION, AND THERAPEUTIC COMPOSITIONS CONTAINING SAME

[75] Inventors: Jacques G. Maillard, Versailles; Tri V. Van, Igny; Jacky M. Legeai, Palaiseau; Marguerite M. Benharkate, Le Perray en Yvelines, all of France

[73] Assignee: Laboratoires Jacques Logeais, Issy les Moulineaux, France

[21] Appl. No.: 571,524

[22] Filed: Jan. 17, 1984

[30] Foreign Application Priority Data

Jan. 28, 1983 [FR] France ................................ 83 01360

[51] Int. Cl.$^4$ ............................................ C07D 207/14
[52] U.S. Cl. ...................................... 514/426; 548/525; 548/526; 548/558; 514/422
[58] Field of Search ........................ 548/558, 526, 525; 424/274; 514/422, 426

[56] References Cited

U.S. PATENT DOCUMENTS

| 3,632,604 | 1/1972 | Eberle et al. | 548/558 |
| 3,725,435 | 4/1973 | Poos | 548/558 X |
| 3,887,569 | 6/1975 | Poos | 548/558 X |

FOREIGN PATENT DOCUMENTS

| 1770752 | 11/1971 | Fed. Rep. of Germany . |
| 2321950 | 11/1973 | Fed. Rep. of Germany . |
| 2227002 | 11/1974 | France . |
| 1527510 | 10/1978 | United Kingdom . |

Primary Examiner—Joseph Paul Brust
Attorney, Agent, or Firm—Young & Thompson

[57] ABSTRACT

This invention relates to therapeutically useful compounds, particularly in the cardiovascular field, having the formula:

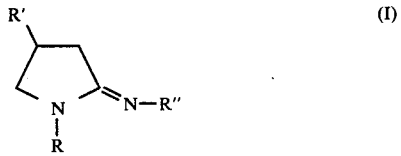

5 Claims, No Drawings

2-IMINO-PYRROLIDINES, PROCESS FOR THEIR PREPARATION, AND THERAPEUTIC COMPOSITIONS CONTAINING SAME

This invention relates to 2-imino-pyrrolidines which are therapeutically useful in the cardiovascular field.

2-Imino-pyrrolidines unsubstituted at 4-position are already known. Thus: DE-A-1770 752 discloses in particular 1-methyl-2-[(3,4-dimethoxy-phenylethyl)imino]-pyrrolidine. This compound (Compound A) is described as having a decreasing action on the cardiac rhythm. As shown by the comparative tests given in the pharmacological part of the disclosure, this compound exhibits neither anti-blood-platelet-aggregation activity nor anti-arrhythmic activity.

The present invention concerns 2-imino-pyrrolidines substituted at 4-position with aromatic type groups.

Thus, this invention relates to compounds of the formula:

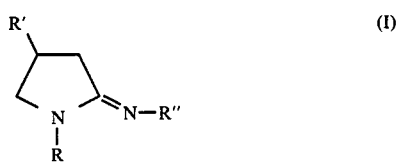

in which:

R represents a $C_{1-4}$ alkyl group, a $C_{2-4}$ alkenyl group, or a $C_2$–$C_4$ alkynyl group;

R' represents a phenyl group optionally substituted with one or more substituents selected from a chlorine atom, a fluorine atom, a $C_{1-4}$ alkyl group, a $C_{1-4}$ alkoxy group, a hydroxy group, a nitrile group or a methylene dioxy group; a 2-benzofuryl group or a phenoxy methyl group optionally substituted on the phenyl moiety with one or more substituents selected from a chlorine atom, a fluorine atom, a $C_{1-4}$alkyl group, a hydroxy group, a cyano group or a methylene dioxy group, R" represents a $C_{1-4}$ alkyl group, a $C_{2-4}$ alkenyl group, a $C_{2-4}$ alkynyl group, a $C_{1-4}$ hydroxyalkyl group, a ($C_{1-4}$alkoxy) ($C_{1-4}$alkyl) group, a phenyl($C_{1-4}$alkyl) or phenoxy($C_{1-4}$alkyl) group optionally substituted on the phenyl moiety with one or more substituents selected from a chlorine atom, a fluorine atom, a $C_{1-4}$alkyl group, a $C_{1-4}$alkoxy group, a hydroxy group, a cyano group or a methylene dioxy group, and their pharmaceutically acceptable acid addition salts.

This invention includes also within its scope therapeutic compositions comprising, as active ingredient, a compound of the formula (I) or a pharmaceutically acceptable acid addition salt thereof.

In the above definition, by "pharmaceutically acceptable acid addition salts" are meant the salts which possess the biological properties of the free bases, while being free from any undesirable effect. Said salts may be those formed with inorganic acids such as hydrochloric acid, hydrobromic acid, sulfuric acid, nitric acid, phosphoric acid, acidic metal salts such as disodium orthophosphate and monopotassium sulfate, and organic acids such as formic acid, acetic acid, propionic acid, glycolic acid, oxalic acid, fumaric acid, citric acid, malic acid, methanesulfonic acid, lactic acid, succinic acid, tartaric acid and pamoic acid.

A preferred class of compounds of the formula (I) is that in which R" represents a substituted or unsubstituted phenyl($C_{1-4}$alkyl) or phenoxy($C_{1-4}$alkyl) group, and more particularly a phenyl($C_{1-4}$alkyl), 3,4-dimethoxy($C_{1-4}$alkyl) and phenoxy($C_{1-4}$alkyl) group.

The compounds of the formula (I) may be prepared by a process comprising:

(a) alkylating a pyrrolidin-2-one of the formula:

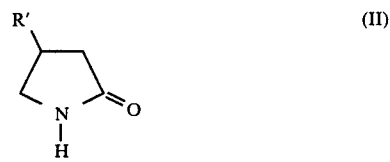

in which R' has the above-defined meaning, to give a pyrrolidin-2-one of the formula:

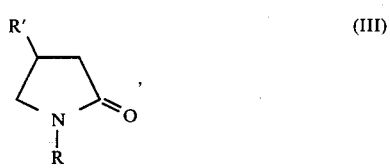

(b) converting the pyrrolidin-2-one of the formula (III) to a 2-alkoxy-Δ2-pyrroline of the formula:

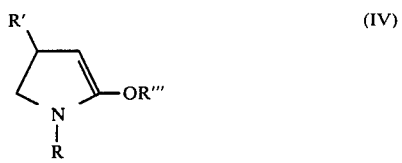

in which R and R' have the above-defined meanings and R" represents a methyl or ethyl group, (c) reacting a 2-alkoxy-Δ2-pyrroline of the formula (IV) with an amine of the formula R"-NH$_2$, to give a compound of the formula (I), and optionally converting the resulting compound of the formula (I) to a pharmaceutically acceptable acid addition salt.

The pyrrolidin-2-ones of the formula (II) are known compounds (Patent FR-A-2 100 946) or may be prepared in the same manner as the known compounds.

The alkylation of the pyrrolidin-2-ones of the formula (II) may be effected in a conventional manner. Thus, a pyrrolidin-2-one of the formula (II) may be reacted with an alkylating agent such as a halide, a sulfate or a tosylate. As the case may be, the reaction may be effected by simple heating or after conversion of the pyrrolidinone to the sodium salt by means of sodium hydride. As a modification, the reaction may be effected in the presence of a quaternary base, according to the conventional phase transfer method.

In the case where the radical R' represents a substituted or unsubstituted phenoxymethyl group, it is advantageous to alkylate a pyrrolidin-2-one of the formula:

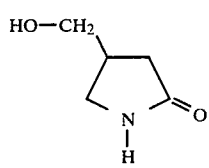

and subsequently to convert the OH group to a phenoxy group, typically via the tosylate and reaction with an alkali metal phenoxide.

The conversion of the pyrrolidin-2-one of the formula (III) to a 2-alkoxy-Δ2-pyrroline of the formula (IV) may be effected by heating with dimethyl sulfate, and then with sodium ethoxide or methoxide.

The conversion may also be effected by action of triethyloxonium tetrafluoroborate (L. F. Fieser & M. Fieser Reagents for Organic Synthesis Wiley, Vol. 1, p.1210) at room temperature, preferably within a chlorinated solvent. In the latter case, the 2-alkoxy-Δ2-pyrroline is generally not isolated, but is directly treated in the next step.

The reaction of 2-alkoxy-Δ2-pyrrolines of the formula (IV) with primary amines R"NH₂ may generally be effected by simply mixing at room temperature.

The following non-limiting Examples illustrate the preparation of compounds of the formula (I).

EXAMPLE 1

1-Methyl-4-phenyl-2-phenylethylimino-pyrrolidine and hydrogenfumarate (I; R=—CH₃; R'=—C₆H₅; R"=—CH₂CH₂C₆H₅)

(a) 1-Methyl-4-phenyl-pyrrolidin-2-one

To a solution of 16.1 g (0.1 mole) 4-phenyl-pyrrolidin-2-one in 40 ml benzene heated to 60°–70° C. are added 12.6 g (0.1 mole) dimethyl sulfate. The mixture is refluxed for 3 hrs. After alkalinisation, the organic phase is decanted off and the aqueous phase is extracted with benzene. The combined benzene phases are dried over sodium hydroxide pellets, and are then evaporated. The residue is distilled under reduced pressure: b.p.$_{10\ mm\ Hg}$=180° C.

Modification, via phase transfer:

A mixture of 4-phenyl-pyrrolidin-2-one (32.2 g; 0.2 mole), dimethyl sulfate (37.8 g; 0.3 mole), tetrabutyl ammonium hydrogensulfate (3.4 g; 0.01 mole), 50% aqueous sodium hydroxide solution (100 ml) and toluene (200 ml) is stirred at 36° C. for 5 hrs. After cooling, the aqueous phase is decanted, extracted with methylene chloride, and combined with the toluene phase. The organic phase is washed with water, dried and evaporated. The residue is distilled: b.p.$_{0.2\ mm\ Hg}$=120° C. Yield: 79%.

(b) 1-Methyl-4-phenyl-2-ethoxy-Δ2-pyrroline

A mixture of the product obtained under (a) (23 g. 0.13 mole) and dimethyl sulfate (16.6 g; 0.13 mole) is stirred at 80° C. for 3 hrs. After the temperature has dropped to 50°–60° C., the mixture is added to a sodium ethoxide solution prepared from 2.9 g sodium in 55 ml absolute ethanol.

The above material is stirred at 50°–60° C. for 6 hrs, after which the ethanol is evaporated off. The residue is distilled under reduced pressure: b.p.(0.1 mm Hg)=104°–114° C.

(c) 1-Methyl-4-phenyl-2-phenylethylimino-pyrrolidine and hydrogenfumarate

A solution containing 11 g (0.54 mole) of the compound obtained in (b) and 5 ml phenylethylamine in 70 ml ethanol is refluxed for 24 hrs. After evaporation of the solvent, the residue is distilled: b.p. (0.1 mm Hg)=166° C. Yield: 67%.

The resulting base is converted to a salt by addition of an equimolar amount of fumaric acid within ethanol under refluxing conditions. The alcohol is evaporated off and the residue is crystallized by addition of ether. M.p.=124° C. Quantitative yield.

EXAMPLE 2

1-Methyl-4-phenyl-2-phenylisopropylimino-pyrrolidine and hydrogenfumarate

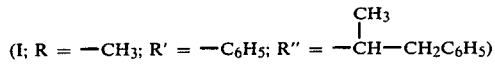

(I; R = —CH₃; R' = —C₆H₅; R" = —CH—CH₂C₆H₅)

The base is prepared as in Example 1, from 1-methyl-4-phenyl-2-ethoxy-Δ2-pyrroline and phenylisopropylamine. B.p. (0.1 mm Hg)=150°–152° C. Yield: 61%.

The base is converted to the hydrogenfumarate as described in Example 1. M.p.=110° C. Yield is quantitative.

EXAMPLE 3

1-Methyl-4-phenyl-2-(2-phenoxy-ethylimino)pyrrolidine and hydrogenfumarate (I; R=—CH₃; R'=—C₆H₅; R"=—CH₂CH₂OC₆H₅)

The base is prepared as in Example 1, from 1-methyl-4-phenyl-2-ethoxy-Δ2-pyrroline and 2-phenoxy-ethylamine. B.p. (0.2 mm Hg)=188°–190° C. Yield: 70%.

The base is converted to the hydrogenfumarate as described in Example 1. M.p.=104° C. Quantitative yield.

EXAMPLE 4

1-Methyl-4-phenyl-2-(3',4'-dimethoxy-phenethylimino)pyrrolidine and hydrogenfumarate

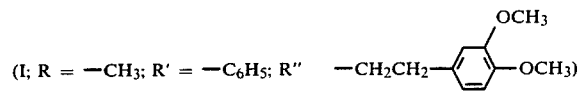

(I; R = —CH₃; R' = —C₆H₅; R"  —CH₂CH₂—⟨C₆H₃⟩(OCH₃)(OCH₃))

The base is prepared as in Example 1, from 1-methyl-4-phenyl-2-ethoxy-Δ2-pyrroline and 3',4'-dimethoxy-phenethyl amine. B.p. (0.2 mm Hg)=216° C. Yield: 59%.

The base is converted to the hydrogenfumarate, as described in Example 1. The salt cristallizes from a mixture of isopropanol and diisopropyl ether. M.p.=216° C. Yield: 75%.

EXAMPLE 5

1-Ethyl-4-phenyl-2-(3',4'-dimethoxy-phenethylimino)-pyrrolidine and phosphate

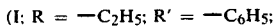

(I; R = —C₂H₅; R' = —C₆H₅;

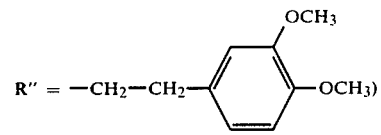

R" = —CH₂—CH₂—⟨C₆H₃⟩(OCH₃)(OCH₃))

(a) 1-Ethyl-4-phenyl-pyrrolidin-2-one

A mixture of 4-phenyl-pyrrolidin-2-one (24.2 g; 0.15 mole) and sodium hydride (80% oil suspension) (5.4 g; 0.18 mole) in tetrahydrofuran (150 ml) is refluxed for 2.5 hrs. After cooling, ethyl iodide (29 g; 0.185 mole) is added thereto, and the resulting material is refluxed for another 5 hrs. The solvent is then evaporated off; the residue is taken up into chloroform, washed with water, dried and distilled. B.p. (0.2 mm Hg)=124°-126° C. Yield: 57%.

(b) and (c)
1-Ethyl-4-phenyl-2-(3',4'-dimethoxyphenethylimino)-pyrrolidine and phosphate A mixture of 1-ethyl-4-phenyl-pyrrolidin-2-one (7.55 g; 0.04 mole), triethyloxonium tetrafluoroborate (8.6 g; 0.04 mole) and methylene chloride (100 ml) is left aside at room temperature for 4 days. After cooling with a water/ice bath, 3',4'-dimethoxy-phenethylamine (9.1 g; 0.05 mole) is added thereto, after which the resulting material is stirred for 3 hrs and then left aside overnight. The mixture is then hydrolyzed by addition of 2.5N aqueous sodium hydroxide (40 ml). The organic phase is decanted off, washed with water, dried over potassium carbonate and distilled. B.p. (0.3 mm Hg)=198° C. Yield: 56%.

The base is converted to the monobasic phosphate by addition of an equimolar amount of phosphoric acid within ethanol. The salt crystallizes after stirring for 2 hrs. M.p.=128° C. Yield: 98%.

EXAMPLE 6

1-n.Propyl-4-phenyl-2-(phenoxyethyl-imino)pyrrolidine and hydrogenfumarate (I; R=—n.C$_3$H$_7$; R'=—C$_6$H$_5$; R"=—CH$_2$CH$_2$O—C$_6$H$_5$)

(a) 1-n.Propyl-4-phenyl-pyrrolidin-2-one

The compound is prepared by action of n.propyl bromide on 4-phenyl-pyrrolidin-2-one, in the presence of sodium hydride, as described in Example 5. B.p. (0.3 mm Hg)=128°-130° C. Yield: 62%.

(b) and (c)
1-n.Propyl-4-phenyl-2-(phenoxyethylimino)-pyrrolidine and hydrogenfumarate The base is prepared from 1-propyl-4-phenyl-pyrrolidin-2-one, by the successive actions of triethyloxonium tetrafluoroborate and of phenoxyethylamine, as described in Example 5. B.p. (0.2 mm Hg)=186°-187° C. Yield: 98%.

The base is converted to the hydrogenfumarate, as described in Example 1. M.p.=126° C. Yield: 98%.

EXAMPLE 7

1-Allyl-4-phenyl-2-(3',4'-dimethoxy-phenethyl-imino)-pyrrolidine and phosphate (I; R = —CH$_2$CH=CH$_2$; R' = —C$_6$H$_5$;

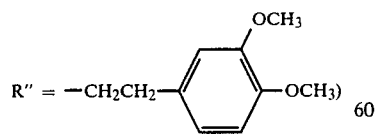

R" = —CH$_2$CH$_2$—⟨phenyl with OCH$_3$, OCH$_3$⟩)

(a) 1-Allyl-4-phenyl-pyrrolidin-2-one

The compound is prepared by action of allyl bromide on 4-phenyl-pyrrolidin-2-one, in the presence of sodium hydride, as described in Example 5. B.p. (0.3 mm Hg)=128° C. Yield: 75%.

(b) and (c)
1-Allyl-4-phenyl-2-(3',4'-dimethoxyphenethyl-imino)-pyrrolidine and phosphate.

The base is prepared by the successive actions of triethyloxonium tetrafluoroborate and of 3',4'-dimethoxyphenethylamine on 1-allyl-4-phenyl-pyrrolidin-2-one, as described in Example 5. B.p. (0.3 mm Hg)=222°-224° C. Yield: 70%.

The base is converted to the monobasic phosphate as in Example 5. M.p.=106° C.

EXAMPLE 8

1-Methyl-4-(2-benzofuryl)-2-n.propyl-imino-pyrrolidine and hydrogenfumarate

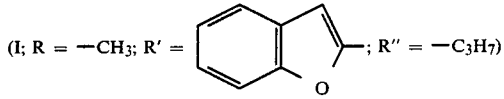

(I; R = —CH$_3$; R' = ⟨benzofuryl⟩; R" = —C$_3$H$_7$)

(a) 1-Methyl-4-(2-benzofuryl)-pyrrolidin-2-one

The compound is prepared from 4-(2-benzofuryl)-pyrrolidin-2-one, sodium hydride and methyl iodide, as described in Example 5. B.p. (0.3 mm Hg)=172° C. M.p. 73° C. Yield: 81%.

(b) and (c)
1-Methyl-4-(2-benzofuryl)-2-n.propyl-imino-pyrrolidine and hydrogen fumarate The base is prepared from 1-methyl-4-(2-benzofuryl)-pyrrolidin-2-one by the successive actions of triethyl oxonium tetrafluoroborate and of n.propylamine as described in Example 5. B.p. (0.2 mm Hg)=150°-152° C. Yield: 78%.

The base is converted to the hydrogenfumarate as in Example 1. Yield: 86%.

EXAMPLE 9

1-Methyl-4-(2-benzofuryl)-2-allylimino-pyrrolidine and hydrogenfumarate (I; R = —CH$_3$; R' = 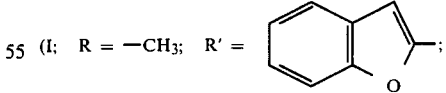;

R" = —CH$_2$CH=CH$_2$)

The base is prepared from 1-methyl-4-(2-benzofuryl)-pyrrolidin-2-one, by the successive actions of triethyl oxonium tetrafluoroborate and of allylamine, as described in Example 5. B.p. (0.1 mm Hg)=156°-158° C. Yield: 85%.

The base is converted to the hydrogenfumarate as in Example 1. M.p.=136° C. Yield: 89%.

EXAMPLE 10

1-Methyl-4-(2-benzofuryl)-2-propargylimino-pyrrolidine and hydrogenfumarate

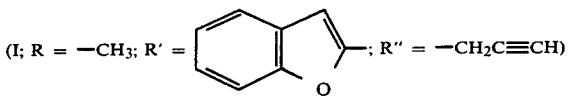

(I; R = —CH$_3$; R' = [benzofuryl]; R" = —CH$_2$C≡CH)

The base is prepared from 1-methyl-4-(2-benzofuryl)-pyrrolidin-2-one, by the successive actions of triethyl oxonium tetrafluoroborate and of propargylamine, as described in Example 5. B.p. (0.3 mm Hg)=168°–170° C. Yield: 72%.

The base is converted to the hydrogenfumarate, as in Example 1. M.p.=152° C. Yield=76%.

EXAMPLE 11

1-Methyl-4-(2-benzofuryl)-2-(2-hydroxy-ethylamino)-pyrrolidine and hydrogenfumarate

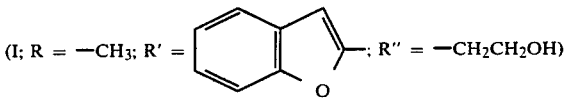

(I; R = —CH$_3$; R' = [benzofuryl]; R" = —CH$_2$CH$_2$OH)

The base is prepared from 1-methyl-4-(2-benzofuryl)-pyrrolidin-2-one, by the successive actions of triethyl oxonium tetrafluoroborate and of 2-hydroxy-ethylamine, as described in Example 5. B.p. (0.5 mm Hg)=184° C. Yield: 52%.

The base is converted to the hydrogenfumarate, recrystallized from isopropanol. M.p.=121° C. Yield: 56%.

EXAMPLE 12

1-Methyl-4-(2-benzofuryl)-2-(2-methoxy-ethylimino)-pyrrolidine and hydrogenfumarate

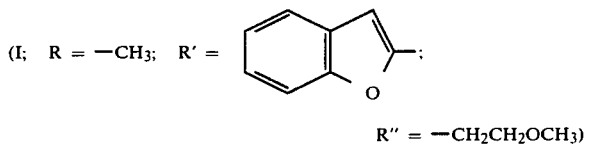

(I; R = —CH$_3$; R' = [benzofuryl]; R" = —CH$_2$CH$_2$OCH$_3$)

The base is prepared from 1-methyl-4-(2-benzofuryl)-pyrrolidin-2-one, by the successive actions of triethyl oxonium tetrafluoroborate and of 2-methoxy-ethylamine, as in Example 5. B.p. (0.1 mm Hg)=168°–170° C. Yield: 78%.

The base is converted to the hydrogenfumarate as in Example 1. M.p.=136° C. Yield: 87%.

EXAMPLE 13

1-Methyl-4-(2-benzofuryl)-2-phenethylimino-pyrrolidine and methanesulfonate

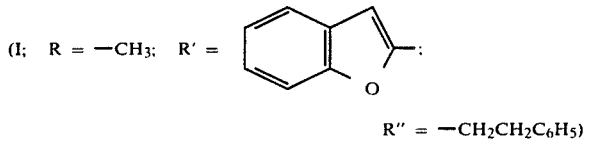

(I; R = —CH$_3$; R' = [benzofuryl]; R" = —CH$_2$CH$_2$C$_6$H$_5$)

The base is prepared from 1-methyl-4-(2-benzofuryl)-pyrrolidin-2)one by the successive actions of triethyl oxonium tetrafluoroborate and of phenethylamine, as in Example 5. B.p. (0.1 mm Hg)=200°–202° C.

The base is converted to the methanesulfonate by addition of a slight deficiency of acid within ethyl acetate from which the salt crystallizes. Yield: 86%.

EXAMPLE 14

1-Methyl-4-(2-benzofuryl)-2-phenylisopropyl-imino-pyrrolidine and methane sulfonate

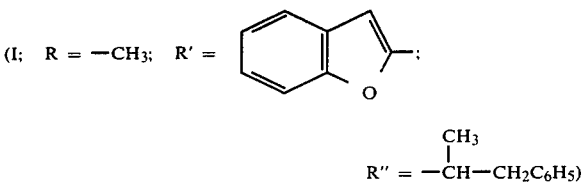

(I; R = —CH$_3$; R' = [benzofuryl]; R" = —CH(CH$_3$)—CH$_2$C$_6$H$_5$)

The base is prepared from 1-methyl-4-(2-benzofuryl)-pyrrolidin-2-one, by the successive actions of triethyl oxonium tetrafluoroborate and of phenylisopropylamine, as in Example 5. B.p. (0.1 mm Hg)=180°–185° C. Yield: 66%.

The base is converted to the methanesulfonate as described in Example 13. M.p.=172° C.

EXAMPLE 15

1-Methyl-4-(2-benzofuryl)-2-(2-phenoxy-ethylimino)-pyrrolidine and hydrogenfumarate

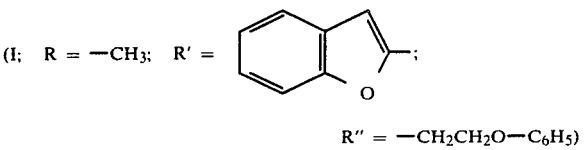

(I; R = —CH$_3$; R' = [benzofuryl]; R" = —CH$_2$CH$_2$O—C$_6$H$_5$)

The base is prepared from 1-methyl-4-(2-benzofuryl)-pyrrolidin-2-one by the successive actions of triethyl oxonium tetrafluoroborate and of 2-phenoxy-ethylamine as in Example 5. B.p. (0.2 mm Hg)=212°–218° C. Yield: 73%.

The base is converted to the hydrogenfumarate, as in Example 1. M.p.=129° C. Yield: 90%.

EXAMPLE 16

1-Methyl)-4-(2-benzofuryl)-2-(3',4'-dimethoxyphenethyl-imino)pyrrolidine and hydrogenfumarate

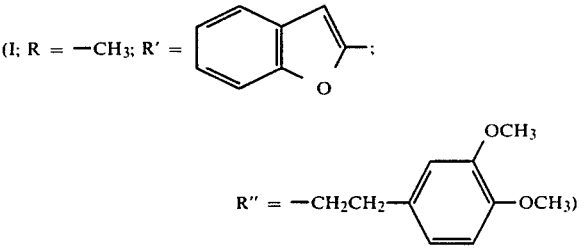

(I; R = —CH$_3$; R' = [benzofuryl]; R" = —CH$_2$CH$_2$—[3',4'-dimethoxyphenyl])

The base is prepared from 1-methyl-4-(2-benzofuryl)-pyrrolidin-2-one by the successive actions of triethyl oxonium tetrafluoroborate and of 2-(3',4'-dimethoxyphenyl)-ethylamine, as in Example 5. B.p. (0.1 mm Hg)=226° C. Yield: 93%.

The base is converted to the hydrogenfumarate as in Example 1. M.p.=106° C. Yield: 93%.

EXAMPLE 17

1-Methyl-4-phenoxymethyl-2-(2-phenoxy-ethylimino)-pyrrolidine and hydrogenfumarate (I; R=—CH$_3$; R'=—CH$_2$—O—C$_6$H$_5$; R"=—CH$_2$CH$_2$O—C$_6$H$_5$)

(a) 1-Methyl-4-phenoxymethyl-pyrrolidin-2-one

1-Methyl-4-tosyloxymethyl-pyrrolidin-2-one is first prepared by action of p.toluenesulfonyl chloride (110 g; 0.58 mole) on 1-methyl-4-hydroxymethyl-pyrrolidin-2-one (68 g; 0.53 mole) in pyridine (170 ml), while cooling to 10° C. After 10 hrs at room temperature, the mixture is hydrolyzed over ice and extracted with methylene chloride. Evaporation of the solvent leaves a crystalline residue. M.p.=66° C. Yield: 76%.

A solution of the resulting tosylate (21.5 g; 0.075 mole) and of potassium phenoxide (10 g; 0.075 mole) in dimethylformamide (150 ml) is refluxed for 2 hrs.

After concentration to dryness in vacuo, the residue is taken up into methylene chloride, washed with water, dried and distilled. B.p. (0.3 mm Hg)=154°–156° C. Yield: 79%.

(b) and (c)
1-Methyl-4-phenoxymethyl-2-(2-phenoxyethylimino)-pyrrolidine and hydrogenfumarate.

The base is prepared from the pyrrolidin-2-one obtained in step (a), by the successive actions of triethyloxonium tetrafluoroborate and of 2-phenoxy-ethylamine as described in Example 5. B.p. (0.3 mm Hg)=210° C. Yield=58%.

The base is converted to the hydrogenfumarate, as described in Example 1. M.p.=144° C. Yield: 94%.

EXAMPLE 18

1-Methyl-4-phenoxymethyl-2-(3',4'-dimethoxy-phenethylimino)pyrrolidine and phosphate (I; R = —CH$_3$; R' = —CH$_2$—O—C$_6$H$_5$;

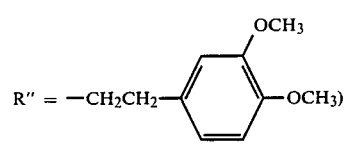

The base is prepared from 1-methyl-4-phenoxymethyl-pyrrolidin-2-one by the successive actions of triethyl oxonium tetrafluoroborate and of 3',4'-dimethoxyphenethyl amine, as described in Example 5. B.p. (0.3 mm Hg)=230° C. Yield: 62%.

The base is converted to the monobasic phosphate, as described in Example 5. M.p.=230° C. (dec.); Yield: 62%.

EXAMPLE 19

1-Methyl-4-(3',4'-methylene dioxy-phenoxymethyl)-2-(2-phenoxy-ethylimino)-pyrrolidine and hydrogenfumarate (I; R = —CH$_3$; R' = 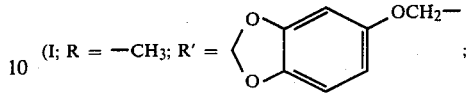 ;

R" = —CH$_2$CH$_2$O—C$_6$H$_5$)

(a) 1-Methyl-4-(3',4'-methylene dioxy-phenoxymethyl)-pyrrolidin-2-one

The compound is prepared from 1-methyl-4-tosyloxy methyl-pyrrolidin-2-one described in Example 17 and potassium 3,4-methylene dioxy-phenoxide, as described in Example 17. B.p. (0.2 mm Hg)=190° C. Yield: 69%.

(b) and (c) 1-Methyl-4-(3',4'-methylene dioxy-phenoxymethyl)-2-(2-phenoxy-ethylimino)pyrrolidine and hydrogenfumarate The base is prepared from the pyrrolidinone obtained in step (a) by the successive actions of triethyloxonium tetrafluoroborate and of 2-phenoxy-ethylamine, as described in Example 5. B.p. (0.2 mm Hg)=200° C. Yield: 73%.

The base is converted to the hydrogenfurarate, as described in Example 1. M.p.=148° C. Yield: 78%.

EXAMPLE 20

1-Methyl-4-(3',4'-methylenedioxy-phenoxymethyl)-4-(3',4'-dimethoxy-phenethylimino)pyrrolidine and phosphate (I; R = —CH$_3$; R' = 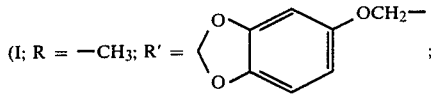 ;

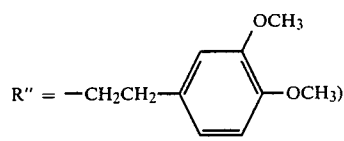

The base is prepared from the pyrrolidinone described in Example 19, by the successive actions of triethyl oxonium tetrafluoroborate and of 3',4'-dimethoxy-phenethyl amine, as described in Example 5. B.p. (0.3 mm Hg)=256° C. Yield: 66%.

The base is converted to the monobasic phosphate, as in Example 5. M.p.=211° C. Yield: 80%.

EXAMPLE 21

1-Methyl-4-(2'-ethyl-phenoxymethyl)-2-(3',4'-dimethoxy-phenethylimino)pyrrolidine and phosphate (I; R = —CH$_2$; R' = 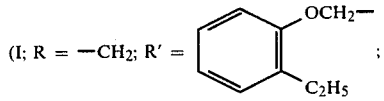 ;

-continued

R″ = —CH₂CH₂— 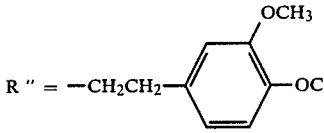

(a) 1-Methyl-4-(2′-ethyl-phenoxymethyl)-pyrrolidin-2-one

The compound is prepared from 1-methyl-4-tosyloxymethyl-pyrrolidin-2-one described in Example 17, and potassium 2-ethyl-phenoxide, as described in Example 17. B.p. (0.3 mm Hg)=186° C.

(b) and (c) 1-Methyl-4-(2′-ethyl-phenoxymethyl)-2-(3′,4′-dimethoxy-phenethylimino)-pyrrolidine and phosphate The base is prepared from the pyrrolidinone obtained in step (a), by the successive actions of triethyloxonium tetrafluoroborate and of 3′,4′-dimethoxy-phenethylamine, as in Example 5. B.p. (0.2 mm Hg)=224° C. Yield: 49%.

The base is converted to the monobasic phosphate as in Example 5. M.p.=208° C. Yield: 91%.

EXAMPLE 22

1-Methyl-4-(2′-cyano-phenoxymethyl)-2-(2-phenoxyethylimino)-pyrrolidine and hydrogenfumarate

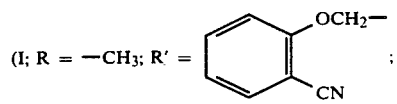

(I; R = —CH₃; R′ = ; R″ = —CH₂CH₂O—C₆H₅)

(a) 1-Methyl-4-(2′-cyano-phenoxymethyl)pyrrolidin-2-one

The compound is prepared from the 4-toxyloxymethyl-pyrrolidin-2-one described in Example 17 and sodium 2-cyanophenoxide, as described in Example 17. B.p. (0.2 mm Hg)=196° C. Yield: 68%.

(b) and (c) 1-Methyl-4-(2′-cyano-phenoxymethyl)-2-(2-phenoxyethylimino)pyrrolidine and hydrogenfumarate The base is prepared from the pyrrolidinone obtained in step (a), by the successive actions of triethyloxonium tetrafluoroborate and of 2-phenoxy-ethylamine, as in Example 5.

The base is converted to the hydrogenfumarate as described in Example 1. M.p.=160° C. Overall yield: 52%.

EXAMPLE 23

1-Methyl-4-(3-methoxy-phenyl)-2-(2-phenoxyethylimino)pyrrolidine and hydrogenfumarate

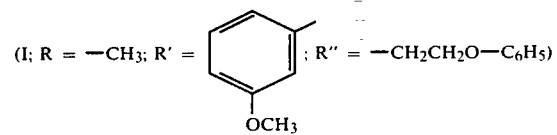

(a) 4-(3-Methoxy-phenyl)-pyrrolidin-2-one

The compound is prepared in the same manner as the pyrrolidin-2-ones of the formula (II) described in FR-A-2 100 946.

(b) 1-Methyl-4-(3-methoxy-phenyl)pyrrolidin-2-one

The compound is prepared by methylation of the preceding pyrrolidin-2-one, according to the process described in Example 1. B.p. (0.4 mm Hg)=150° C. Yield: 73%.

(c) 1-Methyl-4-(3-methoxy-phenyl)-2-(2-phenoxyethylimino)pyrrolidine and hydrogenfumarate The base is prepared from the pyrrolidinone obtained in (b), by the successive actions of triethyl oxonium tetrafluoroborate and of 2-phenoxy-ethylamine, as described in Example 5. B.p. (0.3 mm Hg)=209° C. Yield: 46%.

The base is converted to the hydrogenfumarate, as described in Example 1. M.p.=142° C. Yield: 89%.

EXAMPLE 24

1-Methyl-4-(2-chloro-phenyl)-2-(2-phenoxyethylimino)-pyrrolidine and hydrogenfumarate

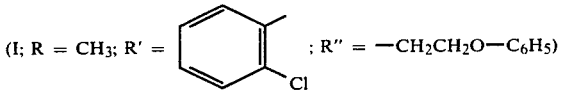

(I; R = CH₃; R′ = ; R″ = —CH₂CH₂O—C₆H₅)

(a) 4-(2-Chloro-phenyl)-pyrrolidin-2-one

The compound is prepared in the same manner as the pyrrolidin-2-ones of the formula (II) described in FR-A-2 100 946.

(b) 1-Methyl-4-(2-chloro-phenyl)-pyrrolidin-2-one

The compound is prepared by methylation of the preceding pyrrolidin-2-one, according to the process described in Example 1. B.p. (0.3 mm Hg)=132° C. Yield: 74%.

(c) 1-Methyl-4-(2-chloro-phenyl)-2-(2-phenoxyethylimino)-pyrrolidin-2-one and hydrogenfumarate The base is prepared from the pyrrolidinone obtained in (b), by the successive actions of triethyl oxonium tetrafluoroborate and of 2-phenoxy-ethylamine, as described in Example 5. B.p. (0.1 mm Hg)=192° C. Yield: 42%.

The base is converted to the hydrogenfumarate, as described in Example 1. M.p.=170° C. Yield: 92%.

EXAMPLE 25

1-Methyl-4-(4-fluoro-phenyl)-2-(2-phenoxyethylimino)-pyrrolidine and hydrogenfumarate

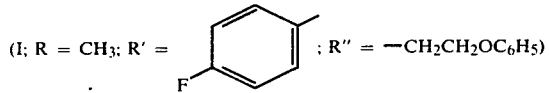

(I; R = CH₃; R′ = ; R″ = —CH₂CH₂OC₆H₅)

(a) 4-(4-Fluoro-phenyl)-pyrrolidin-2-one

The compound is prepared in the same manner as the pyrrolidin-2-ones of the formula (II) described in FR-A-2 100 946.

(b) 1-Methyl-4-(4-fluoro-phenyl)-pyrrolidin-2-one

The compound is prepared by methylation of the preceding pyrrolidin-2-one, according to the process described in Example 1. B.p. (0.3 mm Hg)=128° C. Yield: 83%.

(c) 1-Methyl-4-(4-fluoro-phenyl)-2-(2-phenoxyethylimino)-pyrrolidine and hydrogenfumarate The base is prepared from the pyrrolidinone obtained in (b), by the successive actions of triethyl oxonium tetrafluoroborate and of 2-phenoxy-ethylamine, as described in Example 5. B.p. (0.1 mm Hg)=184° C. Yield: 22%.

The base is converted to the hydrogenfumarate, as in Example 1. M.p.=107° C. Yield: 83%.

The compounds of the formulae (I) and their pharmaceutically acceptable acid addition salts possess useful properties on the heart and the blood-vessels.

In particular, they possess an anti-blood-platelet aggregating activity. In addition, in the case of the preferred compounds of the formula (I), i.e., those in which R" is a phenylalkyl or phenoxyalkyl group, there is noted an interesting anti-arrhythmic activity.

On the other hand, the toxicity of said compounds appears only at dosages highly superior to the pharmacologically active dosages, which makes them therapeutically useful, particularly in the field of cardio-vascular diseases, especially for the prevention and the treatment of thrombosis and in the case of the preferred compounds of the formula I in which R" is a phenylalkyl or phenoxyalkyl group for the prevention and the treatment of disorders of the cardiac rhythm.

The results of toxicological and pharmacological tests which demonstrate said properties are given below.

Acute Toxicity in Mice

The compounds were administered orally or intraperitoneally, in the form of a solution in physiological saline (0,9 % NaCl), to male mice of Swiss strain (body weight: 22–25 g). The death rate was recorded 9 days after the treatment. The dosages administered were 10, 30, 100 and 200 mg/kg, respectively. The results obtained are set forth in Table I.

TABLE I

| Salt of Ex. n° | Acute toxicity | | | Salt of Ex. n° | Acute toxicity | | |
|---|---|---|---|---|---|---|---|
| | dosage (mg/kg) | route | death rate | | dosage (mg/kg) | route | death rate |
| 1 | 100 | i.p. | 80% | 14 | 100 | i.p. | 80% |
| | 200 | p.o. | 0% | | 200 | p.o. | 0% |
| 2 | 100 | i.p. | 100% | 15 | 100 | i.p. | 100% |
| | 200 | p.o. | 83% | | 200 | p.o. | 10% |
| 3 | 200 | i.p. | 0% | 16 | 100 | i.p. | 100% |
| | 200 | p.o. | 0% | | 200 | p.o. | 0% |
| 4 | 200 | i.p. | 100% | 18 | 100 | i.p. | 40% |
| | 200 | p.o. | 0% | | 200 | p.o. | 0% |
| 5 | 100 | i.p. | 20% | 19 | 100 | i.p. | 80% |
| | 200 | p.o. | 0% | | 200 | p.o. | 0% |
| 9 | 100 | i.p. | 60% | 20 | 100 | i.p. | 80% |
| | 100 | p.o. | 0% | | 200 | p.o. | 0% |
| 11 | 200 | i.p. | 80% | 21 | 33 | i.p. | 20% |
| | 200 | p.o. | 0% | | 200 | p.o. | 0% |

TABLE I-continued

| Salt of Ex. n° | Acute toxicity | | | Salt of Ex. n° | Acute toxicity | | |
|---|---|---|---|---|---|---|---|
| | dosage (mg/kg) | route | death rate | | dosage (mg/kg) | route | death rate |
| 12 | 100 | i.p. | 100% | 22 | 33 | i.p. | 40% |
| | 200 | p.o. | 0% | | 200 | p.o. | 0% |
| 13 | 100 | i.p. | 100% | A* | 200 | i.p. | 60% |
| | 200 | p.o. | 0% | | 200 | p.o. | 0% |

A* comparative compound: 1-Methyl-2-[(3,4-dimethoxy-phenethyl)-imino]pyrrolidine.

Anti-Blood-Platelet Aggregating Activity

Collagen-induced blood-platelet aggregation

Blood samples were taken from the carotid artery in rabbits, using an anticoagulant (sodium citrate at 3.8%, 1 volume per 9 volumes of blood). The platelet rich plasma (PRP) was obtained by slow centrifugation (1200 RPM for 10 mn), and the platelet poor plasma (PPP) by rapid centrifugation (4500 RPM for 15 mn). The PRP samples were placed in the cell of an aggregometer, incubated at 37° C., after which was added thereto Michaelis buffer containing the test compound (0.04 ml), followed by the aggregating agent (collagen: 0.08 ml of collagen suspension previously incubated at 33° C. for 90 seconds). Blood-platelet aggregation is evidenced by the decrease of the optical density of the PRP (Initial O.D. of the PRP: 100%. Initial O.D. of the PPP=0%.)

The results obtained are set forth in Table II.

TABLE II

| | Collagen-induced blood-platelet aggregation | |
|---|---|---|
| Salt of Example n° | Threshold concentrations (µg/ml) (inhibition of aggregation <50%) | Strongly inhibiting concentrations (µg/ml) (inhibition of aggregation <50%) |
| 1 | | 100 |
| 2 | 10 | 30–100 |
| 3 | 1–3 | 10–100 |
| 4 | 10–30 | 100 |
| 5 | 3–10 | 30–100 |
| 6 | 1–3 | 10–100 |
| 7 | 10 | 30–100 |
| 8 | 10–30 | 100 |
| 9 | 3–10 | 30–100 |
| 10 | 100 | |
| 11 | 10–100 | |
| 12 | 3–30 | 100 |
| 13 | 3–30 | 100 |
| 14 | 3–10 | 30–100 |
| 16 | 10–30 | 100 |
| 17 | 3 | 10–100 |
| 18 | 10–30 | 100 |
| 19 | 3–10 | 30–100 |
| 20 | 10–30 | 100 |
| 21 | 3 | 10–100 |
| 22 | 30 | 100 |
| A | inactive | |

Additionally, a number of compounds were found to possess a fibrinolytic activity.

The following method was used.

Human plasma clots were prepared by recalcification (one drop of calcium thrombase at 20 U/ml per 0.5 ml of plasma), so that the clot formed around the hook of a glass rod. The clots were then suspended in buffered solutions (veronal buffer pH 7.2–7.4) maintained at 37° C. The eventual lysis of the clot is recorded after 24 hrs and 48 hrs incubation.

The results obtained are given in Table III.

TABLE III

| Salt of Example | Concentration (mmoles/ml) inducing lysis of the clot | |
|---|---|---|
| | within 24 hours | within 48 hours |
| 1 | | 10–20 |
| 2 | 20 | |
| 3 | 10–20 | |
| 6 | | 5–10 |
| 7 | | 10–20 |
| 8 | | 20 |
| 13 | 10 | 2.5–5 |
| 18 | | 20 |
| 21 | | 10–20 |
| 22 | 20 | 5–10 |

Anti-Dysrhythmic Activity

Aconitine test in rats

The animals are anesthetized with urethane (1 g/kg i.p.); an aconitine sulfate injection (27.5 µg/kg) is made in the pre-catheterized jugular vein, 30 minutes after administration by the same route of one of the test compounds. The time delay before the appearance of the first burst of dysrhythmia is noted on the electrocardiogram (D2 lead recording) and compared with reference animals. The results obtained are given in Table IV.

TABLE IV

| Salt of Example n° | Aconitine-induced dysrhythmia | | Salt of Example | Aconitine-induced dysrhythmia | |
|---|---|---|---|---|---|
| | dosage mg/kg | percent animals protected | | dosage mg/kg | percent animals protected |
| 1 | 1 | 25% | 16 | 3 | 80% |
| 2 | 1 | 67% | 17 | 10 | 100% |
| 3 | 10 | 83% | 18 | 5 | 100% |
| 4 | 7.5 | 90% | 19 | 2.5 | 25% |
| 13 | 5 | 50% | 20 | 10 | 100% |
| 14 | 5 | 100% | 21 | 7.5 | 100% |
| 15 | 5 | 80% | A | 5 | 0% |

The high usefulness exhibited by the compound of Example 3 is particularly apparent from the above results. This compound, which is the least toxic in mice, possesses an anti-blood-platelet aggregating activity, an anti-arrhythmic activity, a fibrinolytic activity, together with an α-adrenolytic activity (observed in dog after an injection of nor-adrenalin).

This compound is particularly useful in the treatment of cardiovascular problems subsequent to myocardial infarction, or for the prevention of disorders of the cardiac rhythm in high risk patients.

The compounds of the formula (I) and their pharmaceutically acceptable acid addition salts may be administered to humans in the form of pharmaceutical compositions, by the parenteral, oral, rectal or percutaneous route.

For administration by the parenteral route, the therapeutic compositions may consist of salts in aqueous solutions optionally containing a solubilization adjuvant such as benzyl alcohol or propylene glycol, or within an excipient insuring a delayed resorption.

For the other routes of administration, the compositions may typically be formulated as tablets, capsules, microgranules, suppositories, ointments or creams optionally containing as adjuvants the usual excipients for such pharmaceutical formulations.

For oral administration, the compositions may additionally consist of aqueous solutions of water-soluble salts optionally containing a solubilizing adjuvant.

The various compositions may contain 5–500 mg active ingredient per unit dose, according to the type of formulation and the route of administration. The daily dosage regimen may vary from 0.15 to 3 mg/kg, depending on the route of administration and the therapeutic indications.

We claim:

1. A process for the treatment of thrombosis in a human in need of such treatment comprising administering to a human in need thereof an effective amount of a compound selected from the group consisting of a compound of the formula

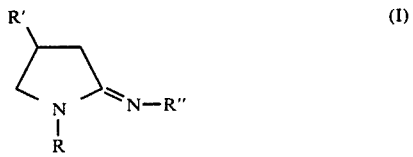

in which:
R is selected from $C_{1-4}$ alkyl; $C_{2-4}$ alkenyl and $C_{2-4}$ alkynyl,
R' is selected from phenyl; phenyl mono-, di- or tri-ring-substituted with substituents selected from chlorine, fluorine, $C_{1-4}$ alkyl, $C_{1-4}$ alkoxy, hydroxy and cyano; methylene dioxy phenyl; 2-benzofuryl; phenoxy methyl; phenoxy methyl mono-, di- or tri-ring-substituted with substituents selected from chlorine, fluorine $C_{1-4}$ alkyl, hydroxy and cyano and methylene dioxy phenoxy methyl,
R" is selected from $C_{1-4}$ alkyl; $C_{2-4}$ alkenyl; $C_{2-4}$ alkynyl; $C_{1-4}$ hydroxyalkyl; ($C_{1-4}$ alkoxy) ($C_{1-4}$ alkyl); phenyl ($C_{1-4}$ alkyl); phenoxy ($C_{1-4}$ alkyl); phenyl ($C_{1-4}$ alkyl) mono-, di- or tri-ring-substituted with substituents selected from chlorine, fluorine, $C_{1-4}$ alkyl, $C_{1-4}$ alkoxy, hydroxy and cyano; methylene dioxy phenyl ($C_{1-4}$ alkyl); phenoxy ($C_{1-4}$ alkyl) mono-, di- or tri-ring-substituted with substituents selected from chlorine, fluorine, $C_{1-4}$ alkyl, $C_{1-4}$ alkoxy, hydroxy and cyano and methylene dioxy phenoxy ($C_{1-4}$ alkyl) and a pharmaceutically acceptable acid addition salt thereof, said amount being effective for the treatment of thrombosis.

2. A process for the treatment of disorders of the cardiac rhythm in a human in need of such treatment comprising administering to a human in need thereof an effective amount of a compound selected from the group consisting of a compound of the formula

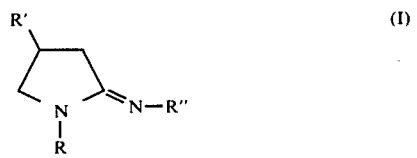

in which:
R is selected from $C_{1-4}$ alkyl; $C_{2-4}$ alkenyl and $C_{2-4}$ alkynyl,
R' is selected from phenyl; phenyl mono-, di- or tri-ring-substituted with substituents selected from chlorine, fluorine, $C_{1-4}$ alkyl, $C_{1-4}$ alkoxy, hydroxy and cyano; methylene dioxy phenyl; 2-benzofuryl; phenoxy methyl; phenoxy methyl mono-, di- or tri-ring-substituted with substituents selected from chlorine, fluorine $C_{1-4}$ alkyl, hydroxy and cyano and methylene dioxy phenoxy methyl, R" is selected from phenyl ($C_{1-4}$ alkyl); phenoxy ($C_{1-4}$ alkyl); phenyl ($C_{1-4}$ alkyl) mono-, di- or tri-ring-substituted with substituents selected from chlorine, fluorine, $C_{1-4}$ alkyl, $C_{1-4}$ alkoxy, hydroxy and cyano; methylene dioxy phenyl ($C_{1-4}$ alkyl); phenoxy ($C_{1-4}$ alkyl) mono-, di- or tri-ring-substituted with substituents selected from chlorine, fluorine, $C_{1-4}$ alkyl, $C_{1-4}$ alkoxy, hydroxy and cyano and methylene dioxy phenoxy ($C_{1-4}$ alkyl) and a pharmaceutically acceptable acid addition salt thereof, said amount being effective for the treatment of disorders of the cardiac rhythm.

3. A process as claimed in claim 2, wherein R" is selected from phenyl ($C_{1-4}$ alkyl), 3,4-dimethoxyphenyl ($C_{1-4}$ alkyl) and phenoxy ($C_{1-4}$ alkyl).

4. A process as claimed in claim 2, in which said compound is 1-methyl-4-phenyl-2-(2-phenoxyethylimino)pyrrolidine or a pharmaceutically acceptable acid addition salt thereof.

5. A process as claimed in claim 2, in which said compound is 1-methyl-4-phenyl-2-(3',4'-dimethoxyphenethylimino) pyrrolidine or a pharmaceutically acceptable acid addition salt thereof.

* * * * *